United States Patent
Yang et al.

(10) Patent No.: US 9,045,450 B2
(45) Date of Patent: Jun. 2, 2015

(54) METHOD FOR CHEMICAL SYNTHESIS OF ANTROCIN AND USE THEREOF FOR SUPPRESSING NON-SMALL CELL LUNG CANCER

(75) Inventors: Zhen Yang, Shenzhen (CN); Yew-Min Tzeng, Taichung (TW); Chuang-Chuang Li, Shenzhen (CN); Tuo-Ping Luo, Newton, MA (US); Hang Shi, Shenzhen (CN); Chi-Tai Yeh, Taipei (TW)

(73) Assignees: Zhen Yang, Shenzhen (CN); Yew-Min Tzeng, Taichung (TW); KAIYEW INVESTMENT CORP., Taichung (TW); JENISA BIOTECHNOLOGY CORP., Taipei (TW)

( * ) Notice: Subject to any disclaimer, the term of this patent is extended or adjusted under 35 U.S.C. 154(b) by 0 days.

(21) Appl. No.: 14/237,569

(22) PCT Filed: Aug. 10, 2011

(86) PCT No.: PCT/CN2011/078232
§ 371 (c)(1),
(2), (4) Date: May 7, 2014

(87) PCT Pub. No.: WO2013/020285
PCT Pub. Date: Feb. 14, 2013

(65) Prior Publication Data
US 2014/0350096 A1 Nov. 27, 2014

(51) Int. Cl.
*C07D 307/88* (2006.01)
*A61K 31/365* (2006.01)

(52) U.S. Cl.
CPC ............ *C07D 307/88* (2013.01); *A61K 31/365* (2013.01)

(58) Field of Classification Search
USPC .................................... 514/468; 549/289, 299
See application file for complete search history.

(56) References Cited

U.S. PATENT DOCUMENTS 8,580,847 B2 * 11/2013 Tzeng et al. .................. 514/468
2011/0263700 A1 10/2011 Tzeng et al.

FOREIGN PATENT DOCUMENTS

CN 102204902 A 10/2011

OTHER PUBLICATIONS

M. Geethangili et al., Review of Pharmacological Effects of Antrodia camphorata and Its Bioactive Compounds, Evidence-based Complementary & Alternative Medicine, vol. 2011, Article ID212641, doi:10.1093/ecam/nep 108.
Rao, Yerra Koteswara et al., Identification of antrocin from *Antrodia camphorata* as a selective and novel class of small molecule inhibitor of Akt/mTOR signaling in metastatic breast cancer MDA-MB-231 cells, Chem Res Toxicol. Feb. 18, 2011;24(2):238-45. doi: 10.1021/tx100318m. Epub Dec. 15, 2010.
Chiang, Hung-Chen et al., A Sesquiterpene Lactone, Phenyl and Biphenyl Compounds from *Antrodia cinnamomea*, Phytochemistry vol. 39, Issue 3, Jun. 1995, pp. 613-616.
International Search Report dated Apr. 23, 2012 from corresponding International Application No. PCT/CN2011/078232.

* cited by examiner

*Primary Examiner* — Kristin Vajda
(74) *Attorney, Agent, or Firm* — Hannah M. Tien

(57) ABSTRACT

The present invention provides a method for preparing antrocin of pharmaceutically acceptable salts thereof via a series of gold-catalyzed cyclization to construct the (6-6-5) tricyclic core frame. The present invention also provides a use of a composition in preparing drugs for suppressing growth of non-small cell lung cancer cells, wherein the composition comprises an effective amount of antrocin or pharmaceutically acceptable salts thereof and a pharmaceutically acceptable carrier.

19 Claims, 7 Drawing Sheets

METHOD FOR CHEMICAL SYNTHESIS OF ANTROCIN AND USE THEREOF FOR SUPPRESSING NON-SMALL CELL LUNG CANCER

BACKGROUND OF THE INVENTION

1. Field of the Invention

The present invention relates to a method for chemical synthesis of antrocin and its use for suppressing non-small cell lung cancer.

2. Description of Prior Art

In the past two decades, studies of natural compounds contained in *Antrodia camphorate* have reported, other than polysaccharides and macromolecules, seventy eight small-molecule compounds, including thirty-one triterpenoids. Most of these studies have provided reports on pharmacological activities of titerpenoids, anti-cancer activities in particular. According to these reports, high dose is required in order for triterpenoids to be clinically effective as chemotherapy drugs used in cancer patients. (Geethangili and Tzeng, Evidence-based Complementary and Alternative Medicine (2011) doi: 10.1093/ecam/nep108). In 1995, antrocin was reportedly found in *Antrodia* for the first time. (Chiang et al., Phytochemistry (1995) 39, 613-616). Since then, there has been no report on antrocin but one, published on Feb. 15, 2011, reporting on its proven efficacy that inhibits breast cancer cell proliferations. (Rao et al., Chemical Research Toxicology (2011) 24, 238-245). No other reports may be found, not even reports on pharmacological activities of antrocin. It may will be that only a trace amount of antrocin may be found in *Antrodia* and it is difficult to isolate antrocin from *Antrodia*.

Lung adenocarcinoma is generally regarded as malignant tumor, a disease. It is characterized by an abnormal mass of malignant tissue resulting from excessive cell division. Unlike normal cells, the proliferation of cancer cells is not regulated resulting in a large number of cancer cells which invade and occupy the space normally reserved for other cells. Common types of cancer treatment include chemotherapy, surgery, radiation therapy and a combination thereof. Chemotherapy is a treatment with one or more chemical compounds which inhibit the growth of cancer cells. Although a number of cancer chemotherapeutic agents have been developed, there remains a need for more effective chemotherapy.

SUMMARY OF THE INVENTION

The present application provides a method for preparing antrocin, comprising the steps of: (a) reacting Compound A with sulfide and haloalkane in the presence of a base to produce an intermediate; and (b) reacting the intermediate with a free radical initiator and a free radical source to form antrocin. The present application also provides a method for suppressing growth of non-small cell lung cancer cells, comprising administering to a subject in need thereof a composition comprising an effective amount of antrocin or pharmaceutically acceptable salts thereof and a pharmaceutically acceptable carrier.

DETAILED DESCRIPTION OF THE INVENTION

Figure 1:
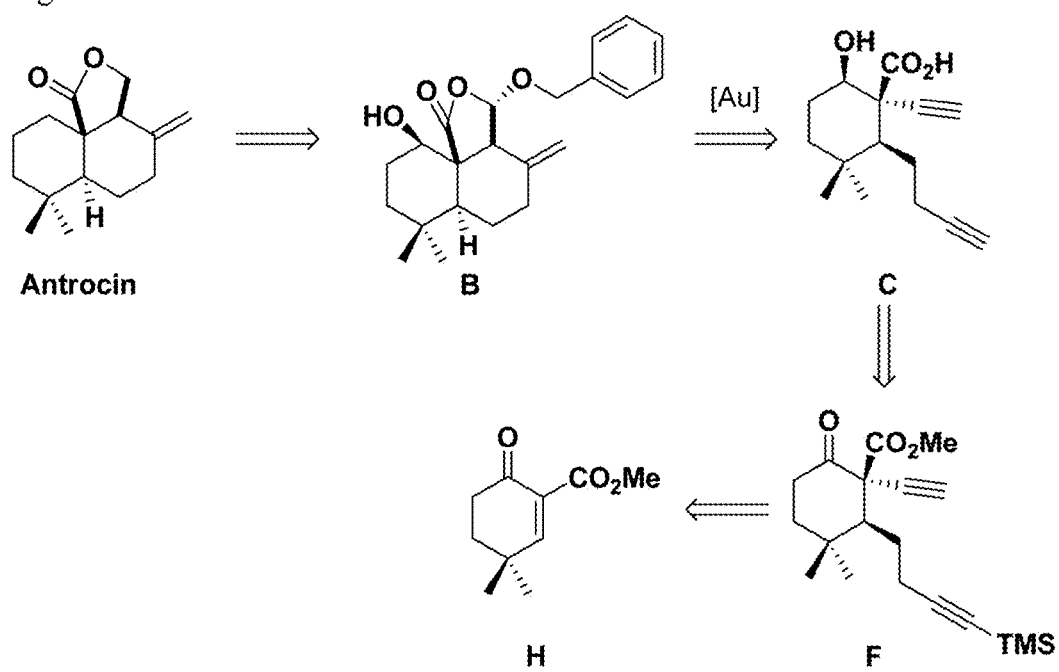
FIG. 1 illustrates a reverse synthetic route of the present invention.

The present invention provides a method for chemical synthesis of antrocin, a natural compound contained in *Antrodia camphorata*,

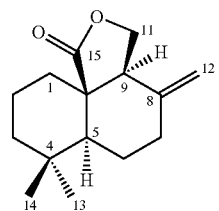

comprising the steps of (a) reacting Compound A

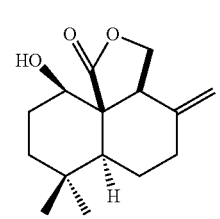

with sulfide and haloalkane in the presence of a base to produce an intermediate; and (b) reacting the intermediate with a free radical initiator and a free radical source to form antrocin, wherein the base is preferably sodium bis(trimethylsilyl)amide, the sulfide is preferably carbon disulfide, the haloalkane is preferably iodomethane, the free radical initiator is preferably azo-bis-isobutyronitrile, and the free radical source is preferably tri-n-butyltin hydride.

Compound A is produced by reacting Compound B

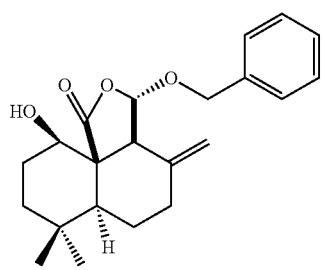

B with an acid via a reducing agent, wherein the reducing agent is preferably an alkali metal, and the acid is preferably hydrochloric acid.

Compound B is produced by reacting Compound C

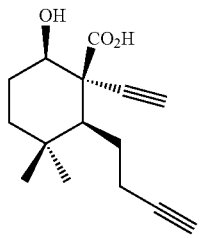

C with alcohol in an organic solvent in the presence of gold compound and silver salt as catalysts, wherein the gold compound is preferably a gold compound (IPr)AuCl having the following structure:

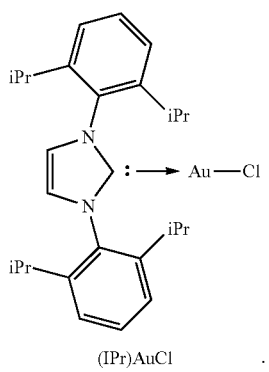

(IPr)AuCl

The silver salt is preferably $AgSbF_6$, the organic solvent is preferably dichloromethane.

Compound C is produced by reacting Compound D

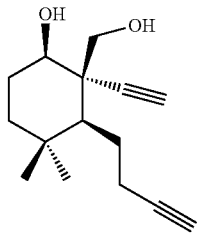

D with a first-step oxidizing agent and then reacting with a second-step oxidizing agent in a cosolvent, wherein the first-step oxidizing agent is preferably (2,2,6,6-tetramethylpiperidin-1-yl)oxy free radical and iodobenzene diacetate, the second-step oxidizing agent is preferably sodium chlorite, and the cosolvent is preferably t-butanol and an aqueous phosphate buffer solution of pH 6.8.

Compound D is produced by reacting Compound E

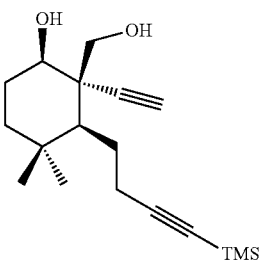

E with a base in a solvent, wherein the base is preferably potassium hydroxide and the solvent is preferably a mixed solvent of methanol, tetrahydrofuran and water.

Compound E is produced by reacting Compound F

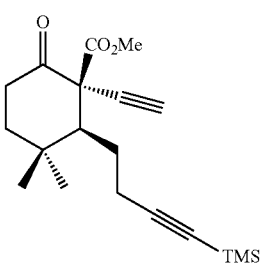

F with a reducing agent, wherein the reducing agent is preferably lithium aluminum hydride.

Compound F is produced by reacting Compound G

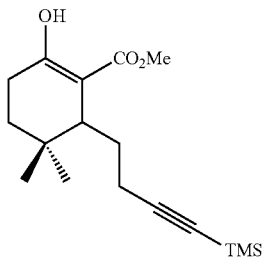

G with hypervalent iodine compound under the effect of a fluorine source, wherein the hypervalent iodine compound is preferably a compound having the following structure:

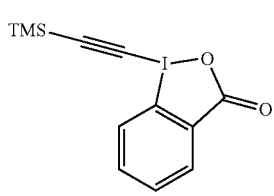 [SMILES: C[Si](C)(C)C#CI1OC(=O)c2ccccc21]

and the fluorine source is preferably tetra-n-butylammonium fluoride in tetrahydrofuran solution.

Compound G is produced by reacting Compound H

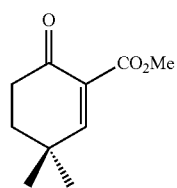

with a Grignard reagent under the effect of a copper reagent, wherein the Grignard reagent is preferably prepared by a bromide having the following structure:

and the copper reagent is preferably cuprous bromide-dimethyl sulfide complex.

The present invention provides a use of a composition in preparing drugs for suppressing growth of non-small cell lung cancer cells. The composition comprises an effective amount of antrocin or a pharmaceutically acceptable salt thereof and a pharmaceutically acceptable carrier. The present invention also provides a method for suppressing cell proliferation of non-small-cell lung cancer cells, comprising administering to a subject in need thereof a composition comprising an effective amount of antrocin or pharmaceutically acceptable salts thereof and a pharmaceutically acceptable carrier. When the composition is used for prevention or treatment of non-small cell lung cancer, the composition has no cytotoxicity against normal human bronchial epithelial cell. Antrocin included in the composition is chemically synthesized in accordance with the method of the present invention. The non-small cell lung cancer cells include CL1-0, CL1-5, A549, PC9, H1975 or H441 cell lines, preferably H441 cell line.

The pharmaceutical composition of the present invention suppresses growth of non-small cell lung cancer cells by activating caspase-3 enzyme path and by suppressing the expression of XIAP, NF-kB and cyclin D1 and reduces gene expression of IFI44, IFIT1, MX1, NFkB1, IFIT2, CTNNBL1, SENP2, CEACAM1, POU5F2, ABCB5, ABCG2 and XAF1 in non-small cell lung cancer cells.

The effective amount of antrocin or pharmaceutically acceptable salts thereof in the pharmaceutical composition of the present invention is 1 mg/kg/day to 50 mg/kg/day, preferably 5 mg/kg/day to 10 mg/kg/day.

Figure 4:
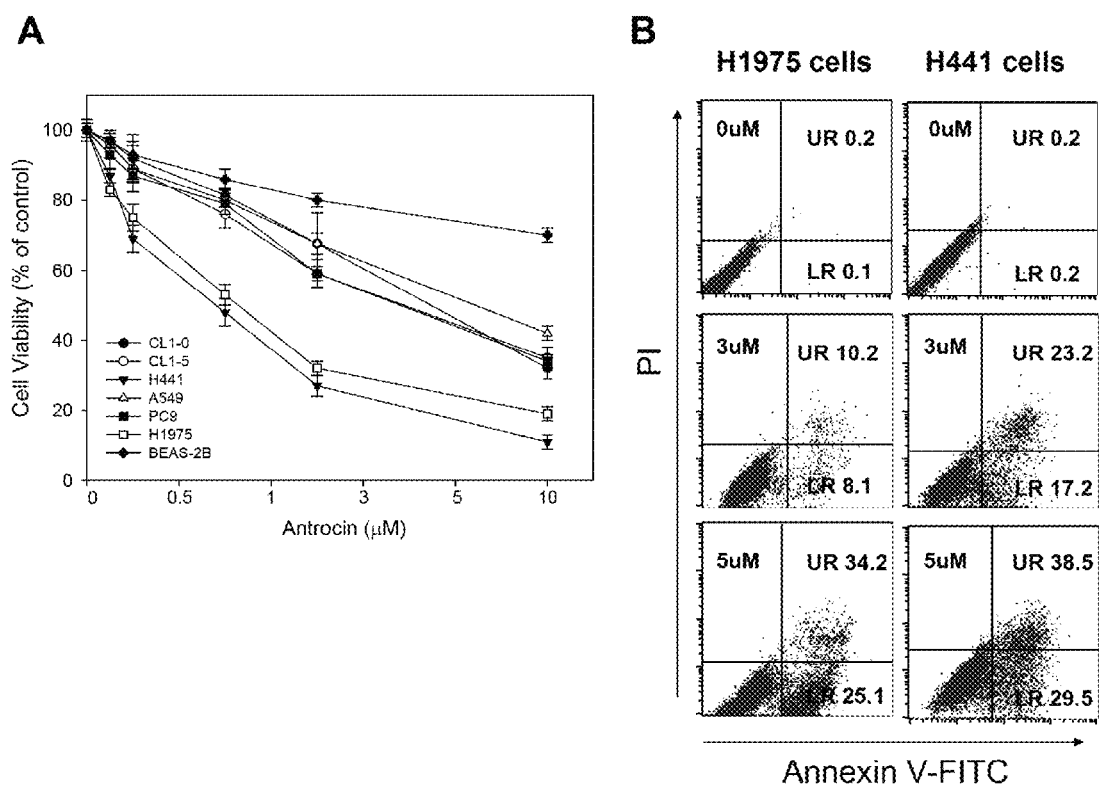
FIG. 4 shows dose-dependent effects of the chemically synthesized antrocin administered to suppress the proliferation of human non-small cell lung cancer cells and to induce apoptosis. Part (A) shows dose-dependent effects of the chemically synthesized antrocin administered to inhibit the proliferation of human non-small cell lung cancer cells and human bronchial epithelial cells. Part (B) shows that the chemically synthesized antrocin induced apoptosis in H1975 and H441 cells.

Previous study has demonstrated that antrocin, a natural compound isolated from *Antrodia*, effectively inhibited cell proliferation in breast cancer cells. (Rao et al., 2011) The present invention aimed to provide a chemically-synthesized antrocin, a natural compound contained in *Antrodia*, and to explore the effect of the chemically-synthesized antrocin on growth of human non-small lung cancer cells. As shown in FIG. 4 (A), the effectiveness of the chemically synthesized antrocin on the inhibition of growth of cancer cell varied in different non-small cell lung cancer cell lines (NSCLC), the most robust inhibitions were observed in H1975 and H441 cell lines. The chemically-synthesized antrocin had significant inhibitory effect on cancer cell proliferation but no cytotoxicity against normal human bronchial epithelial cells.

The present invention further use H1975 and H441 cell lines as models to investigate whether the inhibitory effect of the chemically synthesized antrocin on the cell proliferation was associated with the induction of apoptosis. As shown in FIG. 4 (B), after H1975 and H441 cell lines had been treated with antrocin for 48 hours, the ratio of total number of cells at early and final stage of apoptosis increased significantly in a dose-dependent fashion. The results showed that the chemically synthesized antrocin indeed induced apoptosis in human NSCLC cells.

Figure 5:
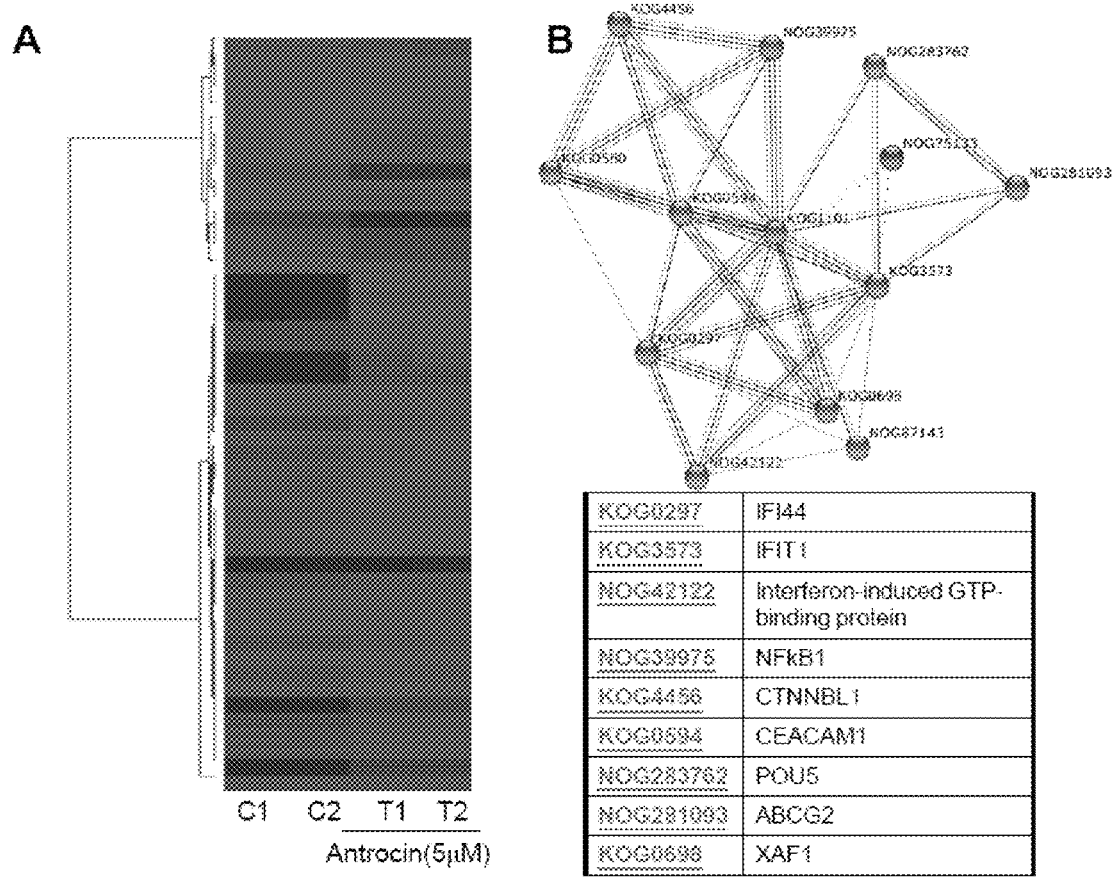
FIG. 5, part (A) is gene mapping of H441 cells treated with antrocin. Dark grey areas represent target genes and light grey areas represent those genes other than the target genes. Part (B) shows the signaling pathway of H441 cells affected by antrocin and possible target genes to be inhibited as predicted by using STRING 9.0 software package.

The present invention further investigated the effect of antrocin on cancer cells at the genetic level. After H441 cells had been treated with 5 µM antrocin for 12 hours, the effect of antrocin on genetic transcription was analyzed. Only those genes whose expressions were inhibited 3.5 times or more were analyzed as target genes by GeneSpring software package and the results were presented using a tree diagram (FIG. 5). The results showed that more than 100 genes whose expressions were significantly affected by the treatment of antrocin. These genes play important roles in cell proliferations, inflammatory responses, metastases, invasions, angiogenesis, and cell cycle regulations. Table 1 summarizes those genes whose expressions were significantly suppressed by the treatment of antrocin. These genes are associated with transcription factor NF-kB, for example cytokines (IFI44, IFIT1, MX1), inflammatory responses (NFkB1 and IFIT2), stem cell properties (CTNNBL1, SENP2, CEACAM1 and POU5F2), and drug resistance reactions (ABCB5, ABCG2 and XAF1), etc. Based on the aforementioned microarray results, the present invention further investigated protein expressions associated with inflammation related factors, stem cell properties, and drug resistance related molecules.

TABLE 1

Genes found in H441 lung cancer cells whose expressions were significantly reduced after antrocin treatment.

| Probe ID | Multiple | Gene Symbol |
|---|---|---|
| 8004184 | 12.61 | *Homo sapiens* XIAP associated factor-1 (XAF1), transcript variant 1, mRNA* |
| 7902541 | 10.74 | *Homo sapiens* mRNA; cDNA DKFZp451O2417 (from clone DKFZp451O2417); complete cds. |
| 8038477 | 10.29 | *Homo sapiens* AKT1 substrate1 (proline rich) (AKT1S1), transcription variant 1, mRNA* |
| 7949532 | 9.93 | *Homo sapiens* FOS-like antigen 1 (FOSL1), mRNA |

TABLE 1-continued

Genes found in H441 lung cancer cells whose expressions were significantly reduced after antrocin treatment.

| Probe ID | Multiple | Gene Symbol |
|---|---|---|
| 8084607 | 8.9 | *Homo sapiens* SUMO1/sentrin/SMT3 specific protease 2 (SENP2), mRNA |
| 7902553 | 8.3 | *Homo sapiens* interferon-induced protein 44 (IFI44), mRNA |
| 7938035 | 7.65 | *Homo sapiens* tripartite motif-containing 22, (TRIM22), mRNA |
| 8011407 | 7.15 | *Homo sapiens* Tax1 (Human T-cell leukemia virus type 1) binding protein (TAX1BP3), mRNA |
| 7937330 | 6.16 | *Homo sapiens* interferon induced transmembrane protein 2 (1-8D) (IFITM2), mRNA |
| 7958913 | 5.91 | *Homo sapiens* 2'-5'-oligoadenylate synthetase 2, 69/71 kDa (OAS2), transcriptvariant 2, mRNA |
| 7971296 | 5.61 | *Homo sapiens* epithelial stromal interaction 1 (breast) (EPSTI1), transcript variant 1, mRNA |
| 8132803 | 5.49 | *Homo sapiens* CDC14 cell division cycle 14 homolog C(*S. cerevisiae*) (CDC14C) on chromosome 7 |
| 8082585 | 5.48 | *Homo sapiens* hypothetical protein FLJ35880 (FLJ35880), mRNA |
| 8068713 | 5.42 | *Homo sapiens* myxovirus (influenza virus) resistance 1, interferon-inducible protein p78 (mouse) (MX1), mRNA |
| 7929065 | 5.28 | *Homo sapiens* interferon-induced protein with tetratricopeptide repeats 1 (IFIT1), transcript variant 2, mRNA |
| 8037205 | 4.99 | *Homo sapiens* carcinoembryonic antigen-related cell adhesion molecule 1 (CEACAM1), transcriptvariant 1, mRNA |
| 8038877 | 4.94 | *Homo sapiens* sialic acid-binding IgG-like lectin 5 (SIGLEC5), mRNA |
| 7906400 | 4.9 | *Homo sapiens* interferon, gamma- inducible protein 16 (IFI16), mRNA |
| 8101126 | 4.62 | *Homo sapiens* chemokine (C-X-C motif) ligand 10 (CXCL10), mRNA |
| 8084732 | 4.6 | *Homo sapiens* receptor (chemosensory) transporter protein (RTP4), mRNA |
| 8039226 | 4.58 | *Homo sapiens* leukocyte immunoglobulin-like receptor, subfamily A (without TM domain), member 3 (LILRA3), mRNA |
| 7929047 | 4.44 | *Homo sapiens* interferon-induced protein with tetratricopeptide repeats 2 (IFIT2), mRNA |
| 8099633 | 4.44 | *Homo sapiens* peroxisome proliferator-activated receptor gamma, coactivator 1 alpha (PPARGC1A), mRNA |
| 8086125 | 4.35 | *Homo sapiens* Lupus brain antigen 1 (LBA1), mRNA |
| 8082100 | 4.3 | *Homo sapiens* poly (ADP-ribose) polymerase family, member 14 (PARP14), mRNA |
| 7973084 | 4.24 | *Homo sapiens* angiogenin, ribonuclease, RNase A family, 5 (ANG), transcript variant 1, mRNA |
| 7967117 | 4.09 | *Homo sapiens* 2'-5'-oligoadenylate synthetase-like (OASL), transcript variant 1, mRNA |
| 8092169 | 4.09 | *Homo sapiens* tumor necrosis factor (ligand) superfamily, member 10 (TNFSF10), mRNA* |
| 8140971 | 4.08 | *Homo sapiens* sterile alpha motif domain containing 9-like, (SAMD9L), mRNA |
| 8090018 | 4.03 | *Homo sapiens* poly (ADP-ribose) polymerase family, member 9 (PARP9), mRNA |
| 8101675 | 3.93 | *Homo sapiens* ATP-binding cassette, subfamily G (WHITE), member 2 (ABCG2), mRNA* |
| 8113094 | 3.9 | *Homo sapiens* POU domain class 5, transcription factor 2 (POU5F2), mRNA |
| 8096635 | 3.85 | *Homo sapiens* nuclear factor of kappa light polypeptide gene enhancer in B-cells 1 (p105) (NFKB1), mRNA* |
| 8163960 | 3.83 | *Homo sapiens* olfactory receptor, family 1, subfamily L, member 8 (OR1L8), mRNA |
| 8092348 | 3.8 | *Homo sapiens* lysosome-associated membrane protein 3 (LAMP3), mRNA |
| 7917276 | 3.75 | *Homo sapiens* endothelial differentiation, lysophosphatidic acid G-protein-coupled receptor, 7 (EDG7), mRNA |
| 8008802 | 3.73 | *Homo sapiens* glycophosphodiester phosphodiesterase domain containing 1 (GDPD1), mRNA |
| 8006531 | 3.65 | *Homo sapiens* schlafen family member 5 (SLFN5), mRNA |
| 8137310 | 3.62 | *Homo sapiens* ATP-binding cassette, subfamily B (MDR/TAP), member 5 (ABCB5), mRNA* |
| 8062409 | 3.59 | *Homo sapiens* catenin, beta like 1 (TNNBL1), mRNA* |
| 8044450 | 3.5 | *Homo sapiens* zinc finger CCCH-type containing 6 (ZC3H6), mRNA |

Figure 6:
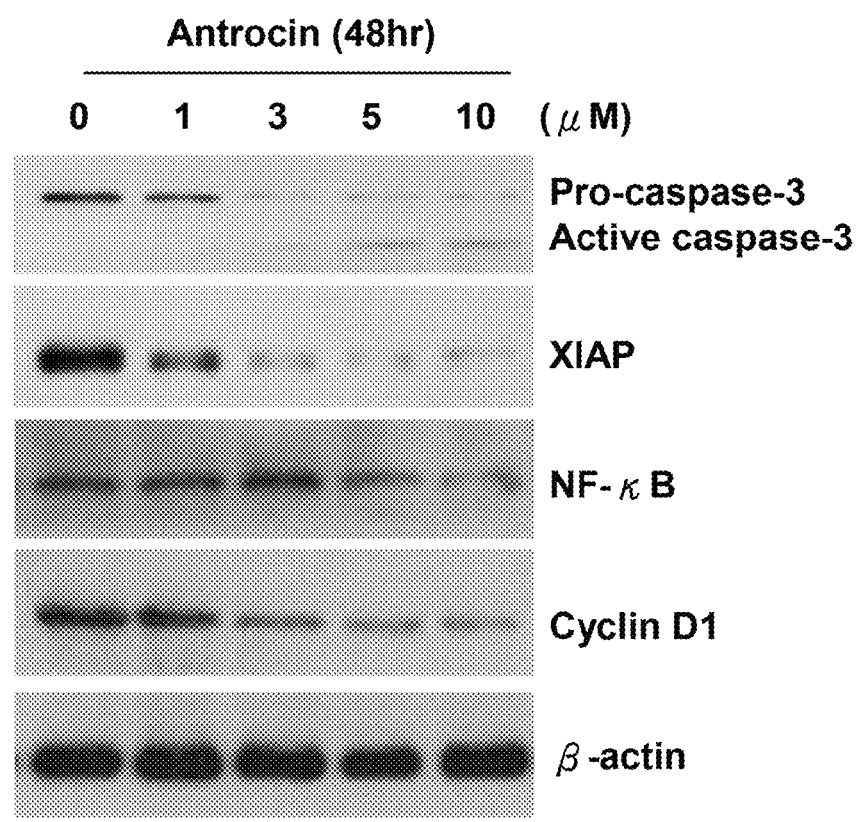
FIG. 6 shows that antrocin inhibits tumorigenesis of H441 cells primarily by activation of caspase-3 enzyme path and inhibition of XIAP, NF-kB and cyclin D1 expressions. The inhibitory effect of antrocin on protein expression is presented as relative multiple.Beta-actin protein was the internal reference (loading control). Three independent experiments showed similar results.

Antrocin inhibited cell proliferation of highly metastatic H441 cells. As the dose increased, antrocin markedly activated caspase enzyme 3, which induced apoptosis in H441 cells (FIG. 6). In addition, antrocin also dose-dependently inhibited the protein expressions associated with inflammatory response related molecules, including XIAP, NF-kB-p65 and cyclin D1.

Figure 7:
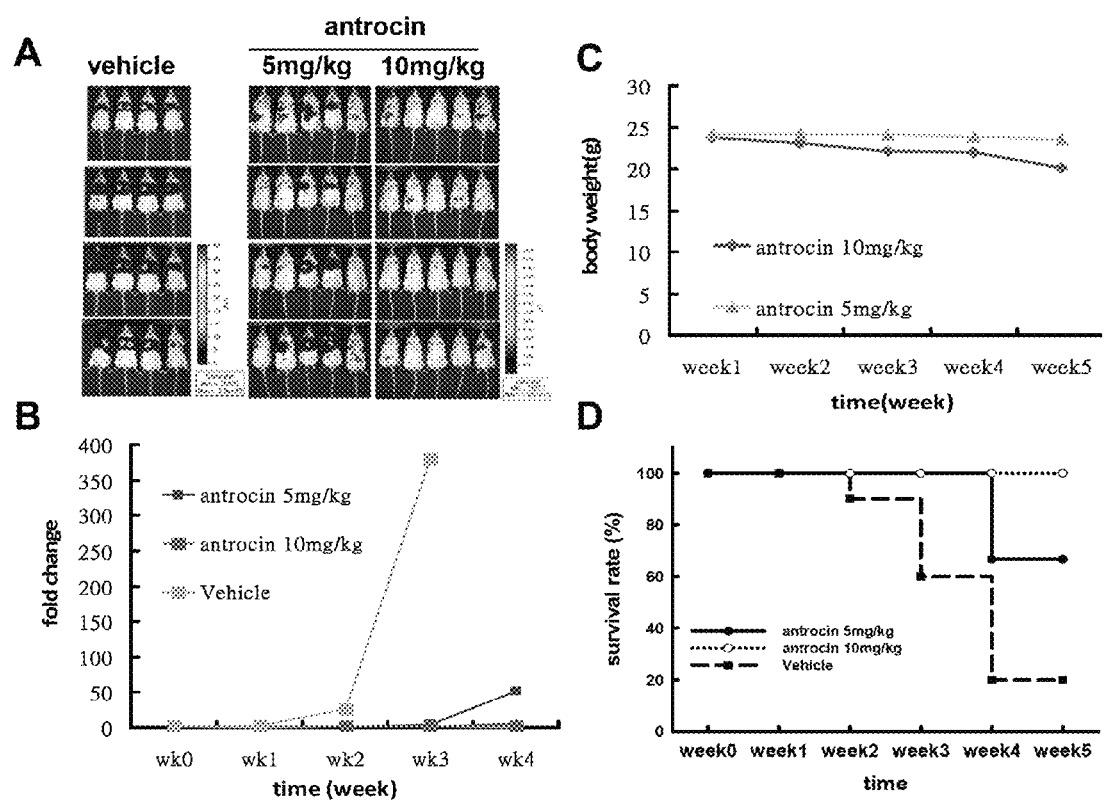
FIG. 7 shows that antrocin inhibits lung tumorigenesis in vivo. H441-2G cells ($6\times10^5$/100 μl PBS) were intravenously injected into immunodeficient mice via lateral tail vein. Antrocin treatments (low dose of 5 mg/kg/day and high dose of 10 mg/kg/day) were performed by daily intraperitoneal injection into tumor-bearing mice over a period of four weeks. Weekly observations were performed and data were recorded for (A) VIS images, (B) Tumor growth, (C) Body weights, and (D) Survival curves.

The present invention further investigated anticancer effect of antrocin in vivo. H441-L2G cells expressing firefly luciferase and green fluorescent protein were implanted by intravenous injections via the lateral tail vein ($6 \times 10^5$/100 µl PBS) into non-obese diabetic/severe combined immunodeficient mice. Daily intraperitoneal injections of antrocin (two groups of mice, a low dose of 5 mg/kg/day and a high dose of 10 mg/kg/day) were given over a period of four weeks to observe tumor growth. Tumor growth was inhibited after two weeks in half of the mice given low dose of antrocin. At the third week, tumor growth was observed in most of these mice (FIG. 7 (A), (B)). There was no significant difference in the body weight between the group treated with antrocin and the control group (FIG. 7 (C)).

With respect to survival rate, the median was 28 days for the control group and longer than 50 days for the treated group. 75% of the mice treated with low dose of antrocin at 5 mg/kg/day survived for longer than 50 days. At the end of the experiment (the fiftieth day) the median survival time increased by at least 60% (FIG. 7 (D)).

Antrocin has one to three chiral centers which may give various stereoisomeric forms of antrocin. Antrocin of the present invention includes all such isomers. Antrocin has selective inhibitory effect on the proliferation of lung adenocarcinoma cells. Low dose of antrocin, in the form of a composition comprising antrocin or its pharmaceutically acceptable salts and a pharmaceutically acceptable carrier, is enough to provide therapeutic effect because of its small molecular weight. The pharmaceutical composition of the present invention may be used to inhibit cancer cell growth and proliferation or may be administered to patients (cancer patients, patients with symptoms of cancer, or those who are prone to cancer) to cure, recover, relieve, alleviate, change, treat, improve, moderate, or affect the disease, the symptoms of the disease, or the physical conditions of those who are prone to cancer. As used herein, an "effective dose" refers to the effective dose of antrocin or its pharmaceutically acceptable salts, an amount that produces a therapeutic response or inhibitory effect. Effective dose may vary depending on the route of administration, excipient and other active agents included in the composition.

As used herein, "lung cancer" refers to lung cell carcinoma. Based on the types of tissue cell, lung cancer may be divided into small-cell lung cancer (SCLC) and non-small cell lung cancer (NSCLC), the latter is the most common type of lung cancer. NSCLC may be further divided into adenocarcinoma and squamous cell carcinoma, most NSCLCs are adenocarcinoma. One feature that characterizes lung cancer is early metastases, which usually occur 5 years after treatment in 50% of patients who suffer from early stage lung cancer. Current TNM staging system is unable to accurately predict lung cancer prognosis. Cancer as used herein includes all types of cancerous growth or oncogenic processes, metastatic tissues or malignant transformation of cells, tissues or organs (unrelated to histopathological features) or any invasive stages.

Antrocin of the present invention is chemically synthesized. In 1995, Antrocin was reportedly found in *Antrodia* for the first time. (Chiang et al., Phytochemistry (1995) 39, 613-616). Since then, there has been no report on Antrocin but one, published on Feb. 15, 2011, reporting on its proven efficacy that inhibits breast cancer cell proliferations. (Rao et al., Chemical Research Toxicology (2011) 24, 238-245). No other reports may be found, not even reports on pharmacological activities of antrocin. It may well be that only a trace amount of antrocin can be found in *Antrodia*, which makes it difficult to isolate antrocin from *Antrodia*.

The present invention discloses that antrocin effectively suppresses cell proliferation of human non-small cell lung cancer cells without being cytotoxic to normal cells (normal human bronchial epithelial cells-BEAS2B). Furthermore, antrocin inhibits cell proliferation in H441 cells by suppressing the expression of inflammatory response-associated proteins, activating caspases-3 enzyme, and suppressing the expression of XIAP, NF-kB-p65 and cyclin D1. Antrocin also significantly inhibits tumor growth in vivo. There are a plurality of natural compounds in *Antrodia camphorate* but antrocin is so far the only one may be synthesized chemically. It is confirmed by experiments in vivo and in vitro that antrocin effectively suppresses the cell proliferation of human non-small cell lung cancer cells.

Antrocin of the present invention or its pharmaceutically acceptable salts may be simultaneously or separately administered orally, parenterally, by inhalation, or by implantation of a reservoir. As used herein, "parenteral" refers to subcutaneous, intracutaneous, intravenous, intramuscular, intraarticular, intraarterial, synovium (cavity), intrasternal, interthecal, intralesional and intracranial and perfusion techniques.

An appropriate dosage form may be formulated by antrocin of the present invention or pharmaceutically acceptable salts thereof and at least one solid, liquid or semi-liquid excipient or adjuvant. The dosage forms include, but are not limited to, tablets, capsules, emulsions, aqueous suspensions, dispersions, and solutions. Carriers commonly used in tablets include lactose and corn starch. Lubricants, such as magnesium stearate, usually are also included in tablets. Diluents used in capsules include lactose and dried corn starch. When the dosage form is aqueous suspension or emulsion and is administered orally, active ingredients may be suspended or dissolved in an oil phase which is combined with emulsifiers or suspending agents. Specific sweetening, flavoring and coloring agents may be added if necessary.

Antrocin of the present invention or pharmaceutically acceptable salts thereof may also be formulated as sterile injectable compositions (e.g., aqueous or oil suspension) by techniques known in the art using suitable dispersing or moisturizing agents (e.g. Tween 80) and suspending agents. Sterile injection may be formulated by adding sterile injectable solutions or suspensions to non-toxic diluents or solvents suitable for parenteral use, for example 1,3-butanediol. Suitable carriers and solvents include mannitols, water, Ringer's solutions and isotonic sodium chloride solutions. In addition, sterile, fixed oils are often used as solvents or suspending media (e.g., synthetic mono- or double-glycerides). Fatty acids, such as oleic acids and its glyceride derivatives, may also be used to formulate sterile injections. Fatty acids are natural pharmaceutically acceptable oils, for example olive oils, castor oils and their polyoxypropylene ethyl forms in particular. These oil solutions or suspensions may also include long-chain alcohol diluents or dispersants, carboxymethyl celluloses or similar dispersing agents.

Antrocin or pharmaceutically acceptable salts thereof may also be formulated by well known techniques in the art into a formula for inhalation. For example, salt solutions may be formulated by using benzyl alcohol or other suitable preservatives, absorption enhancers known to improve bioavailability, fluorocarbons, or other cosolvents or dispensing agents known in the art.

Carriers used in the pharmaceutical composition must be "acceptable", compatible with active ingredients (preferably capable of stabilizing the active ingredients), and no harms to the patients. For example, solubilizers (e.g., cyclodextrin, together with one or more extracts of active compound to form a specific and even more soluble complex) may be used as adjuvant to transfer active ingredients. Other examples of the carrier include colloidal silica, magnesium stearate, cellulose, and sodium dodecyl sulfate.

When high dose of anticancer agents is administered to patients, it tends to cause toxic effects to patients. Accordingly, the pharmaceutical composition of the present invention contains an effective amount of antrocin to suppress cancer cell proliferation, wherein the effective amount of antrocin is from 1 mg/kg/day to 50 mg/kg/day, preferably from 5 mg/kg/day to 10 mg/kg/day. The specific amount of antrocin administered to each individual patient is determined by factors such as the bioactivity of the specific compound to be taken, age, body weight, physical conditions, gender, time and the route of administration, excretion rate, composition of the pharmaceutical substance, severity of the illness to be treated, etc.

EXAMPLES

The examples below further describe the present invention. These examples are non-limiting and are merely representative of various aspects and features of the present invention.

Example 1

Preparation of Antrocin

Unless otherwise specified, all reactions were carried out under $N_2$ protection and anhydrous conditions. All reagents were commercially available from reagent suppliers and used directly without being purified. Reagents were purified in accordance with the guidelines described in Purification of Laboratory Chemicals (Peerrin et al., Pergamon Press: Oxford, 1980). Tetrahydrofuran (THF) and toluene were refluxed with metallic sodium for purification; DCM was purified with $CaH_2$ reflux. Unless otherwise specified, the yield is derived from column chromatography.

Thin layer chromatography silica gel plate (60F-254) manufactured by Qingdao Ocean Chemical Plant was used to carry out reactions and testing. 200-300 mesh silica gel produced by Qingdao Marine Chemical Inc. was used for column chromatography, the boiling range of petroleum ether was 60-90° C.

All infrared data were measured by the following instrument: Shimadzu IRPrestige 21; all nuclear magnetic resonances were measured by the following instrument: Brüker Advance 500 ($^1$H: 500 MHz, $^{13}$C: 125 MHz), TMS or non-deuterated solvent residues left in deuterated solvents was used as the internal standard.

Figure 2:
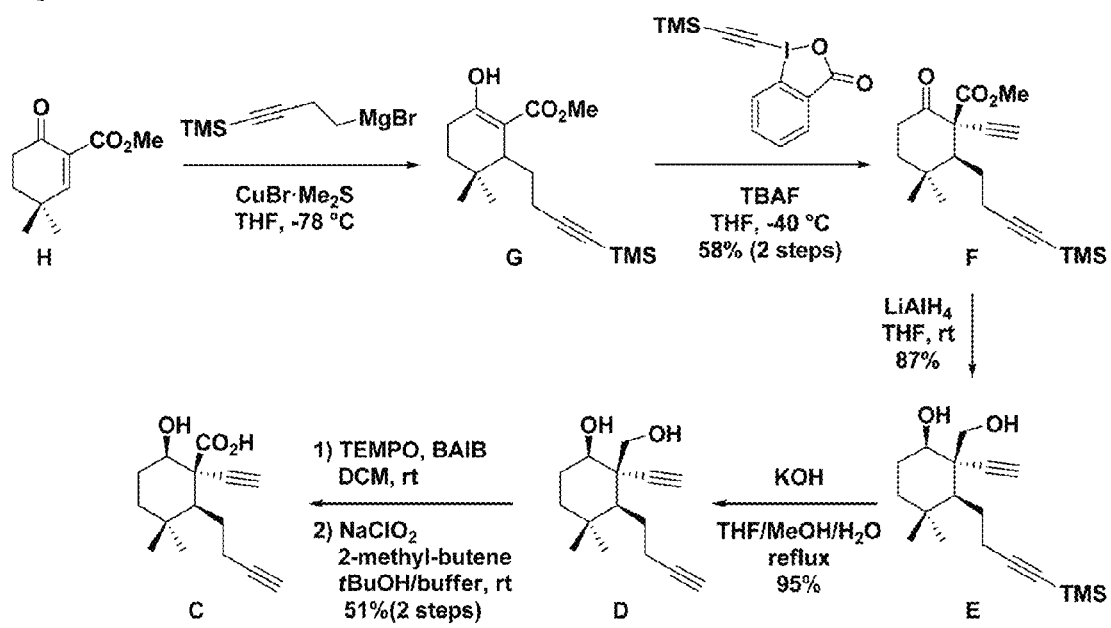
FIG. 2 illustrates a synthetic route of Compound C.
Figure 3:
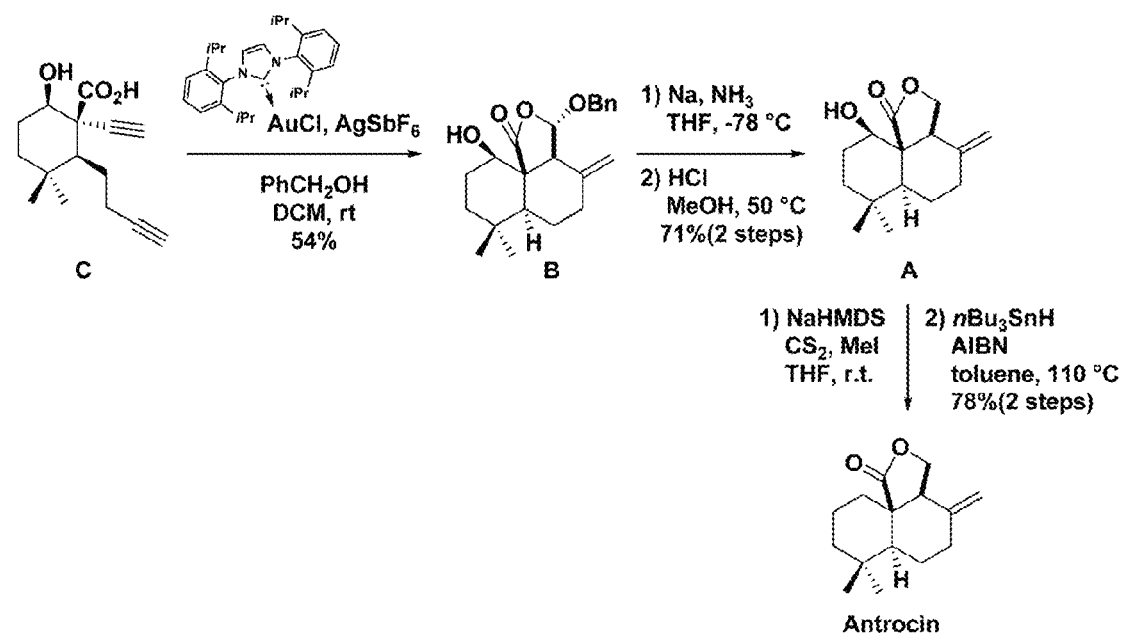
FIG. 3 illustrates the synthetic route of antrocin.

The reaction path of antrocin is shown in FIG. 2 and FIG. 3, and followed the following steps:

Synthesis of Compound F:

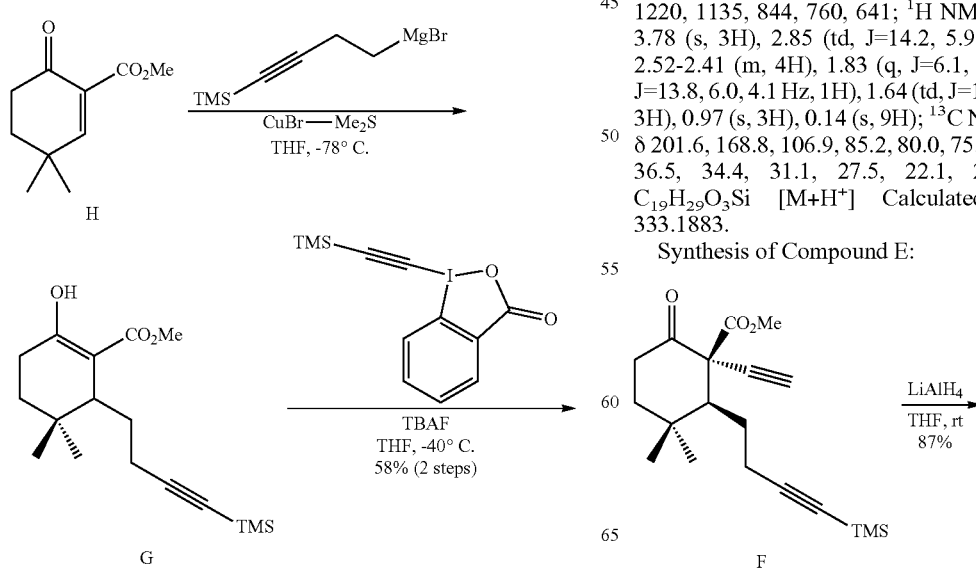

A mixture containing magnesium turnings (0.49 g, 20 mmol) and a small piece of iodine in THF (3 mL) was heated to boiling. Grignard reagent having the following structure was prepared by adding dropwise (4-bromo-but-1-ynyl)trimethylsilane in THF solution (10 mL) to the mixture and continued to stir at room temperature for 0.5 hr to prepare the Grignard reagent with following structure:

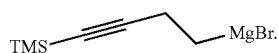

The prepared Grignard reagent was added to a mixture of $CuBr \cdot Me_2S$ (0.32 g, 1.56 mmol) in THF solution (40 mL) at −78° C. Then, a mixture of Compound H (0.95 g, 5.2 mmol) in THF solution (27 mL) was added dropwise. After stirring for two hours, saturated $NH_4Cl$ aqueous solution (50 mL) was added to quench the reaction. The aqueous phase was extracted with EtOAc (40 mL×2), the organic phases were combined and dried, concentrated by rotary evaporation, and purified by column chromatography (EtOAc/hexane=1/100) to yield yellow oily liquid Compound G.

Compound G in THF solution (60 mL) was cooled down to −78° C., hypervalent iodine compound (2.5 g, 7.3 mmol) and TBAF solution (1 M in THF, 7.3 mL, 7.3 mmol) were added. Stirred the solution at −40° C. for four hours and saturated $NH_4Cl$ aqueous solution (50 mL) was added to quench the reaction. The aqueous phase was extracted with EtOAc (40 mL×2), the organic phases were combined and dried, concentrated by rotary evaporation, and purified by column chromatography (EtOAc/hexane=1/20) to yield 1.01 g colorless oily liquid, 58% yield for the two steps.

IR (neat, cm$^{-1}$): 3283, 2960, 2174, 1750, 1727, 1434, 1250, 1220, 1135, 844, 760, 641; $^1$H NMR (500 MHz, CDCl$_3$) δ 3.78 (s, 3H), 2.85 (td, J=14.2, 5.9 Hz, 1H), 2.55 (s, 1H), 2.52-2.41 (m, 4H), 1.83 (q, J=6.1, 5.2 Hz, 2H), 1.74 (ddd, J=13.8, 6.0, 4.1 Hz, 1H), 1.64 (td, J=13.7, 4.5 Hz, 1H), 1.06 (s, 3H), 0.97 (s, 3H), 0.14 (s, 9H); $^{13}$C NMR (126 MHz, CDCl$_3$) δ 201.6, 168.8, 106.9, 85.2, 80.0, 75.9, 60.2, 55.3, 53.2, 40.2, 36.5, 34.4, 31.1, 27.5, 22.1, 20.3, 0.3; HRMS-ESI $C_{19}H_{29}O_3Si$ [M+H$^+$] Calculated: 333.1880; Found: 333.1883.

Synthesis of Compound E:

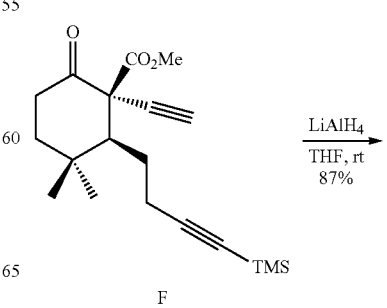

-continued

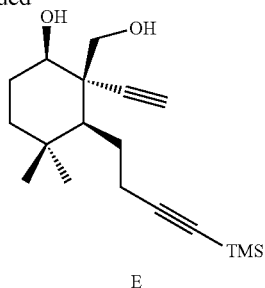

E

LiAlH$_4$ (0.49 g, 12.9 mmol) was added to Compound F (1.07 g, 3.2 mmol) in THF solution (30 mL) at −40° C. Stirred at room temperature for four hours and saturated potassium sodium tartrate solution (20 mL) was used to quench the reaction. The aqueous phase was extracted with EtOAc (20 mL×3), the organic phases were combined and dried, concentrated by rotary evaporation, and purified by column chromatography (EtOAc/hexane=1/3) to yield 0.86 g colorless oily liquid, 87% yield.

IR (neat, cm$^{-1}$): 2958, 2920, 2851, 1261, 1249, 1034, 841, 796, 668; $^1$H NMR (500 MHz, CDCl$_3$) δ 4.14 (dd, J=11.4, 5.8 Hz, 1H), 3.80 (dt, J=11.4, 4.5 Hz, 1H), 3.58 (dd, J=11.3, 7.0 Hz, 1H), 3.02 (d, J=4.7 Hz, 1H), 2.70 (t, J=6.7 Hz, 1H), 2.54 (ddd, J=16.3, 10.2, 5.7 Hz, 1H), 2.39 (ddd, J=16.7, 10.4, 6.0 Hz, 1H), 2.35 (s, 1H), 1.93-1.83 (m, 1H), 1.81 (q, J=4.0 Hz, 1H), 1.75-1.65 (m, 1H), 1.59 (ddd, J=11.8, 6.0, 3.0 Hz, 1H), 1.48 (dt, J=13.9, 3.4 Hz, 1H), 1.39 (t, J=4.3 Hz, 1H), 1.32 (td, J=13.8, 4.1 Hz, 1H), 0.93 (s, 3H), 0.79 (s, 3H), 0.16 (s, 9H); $^{13}$C NMR (126 MHz, CDCl$_3$) δ 107.3, 87.0, 84.8, 79.2, 72.7, 61.5, 52.4, 49.0, 39.4, 34.1, 32.6, 27.5, 26.8, 22.9, 22.3, 0.3; HRMS-ESI C$_{18}$H$_{30}$NaO$_2$Si [M+Na$^+$] Calculated: 329.1907; Found: 329.1903.

Synthesis of Compound D:

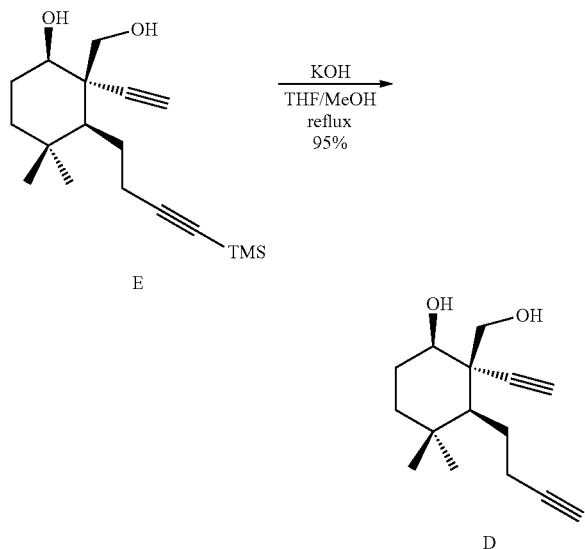

KOH (0.76 g, 13.5 mmol) was added to Compound D (0.84 g, 2.7 mmol) in THF/MeOH/H$_2$O solution (20 mL/10 mL/2 mL) at room temperature. The reaction system was refluxed for 6 hours, cooled to 0° C., saturated NH$_4$Cl aqueous solution (20 mL) was used to quench the reaction. The aqueous phase was extracted with EtOAc (15 mL×2), the organic phases were combined and dried, concentrated by rotary evaporation, and purified by column chromatography (EtOAc/hexane=1/3) to yield 0.6 g colorless oily liquid, 95% yield.

IR (neat, cm$^{-1}$): 3299, 2954, 2878, 2115, 1631, 1464, 1434, 1379, 1056, 998, 634; $^1$H NMR (500 MHz, CDCl$_3$) δ 4.14 (dd, J=11.5, 5.9 Hz, 1H), 3.81 (dt, J=11.3, 4.4 Hz, 1H), 3.58 (dd, J=11.4, 7.0 Hz, 1H), 2.97 (d, J=4.7 Hz, 1H), 2.66 (t, J=6.7 Hz, 1H), 2.51 (dddd, J=13.1, 10.5, 5.7, 2.6 Hz, 1H), 2.41-2.31 (m, 1H), 2.36 (s, 1H), 1.99 (t, J=2.6 Hz, 1H), 1.93-1.79 (m, 2H), 1.76-1.60 (m, 2H), 1.49 (dt, J=13.8, 3.5 Hz, 1H), 1.39 (t, J=4.3 Hz, 1H), 1.33 (td, J=13.7, 4.0 Hz, 1H), 0.93 (s, 3H), 0.80 (s, 3H); $^{13}$C NMR (126 MHz, CDCl$_3$) δ 87.0, 84.5, 79.2, 72.7, 68.6, 61.5, 52.5, 49.0, 39.4, 34.1, 32.5, 27.6, 26.8, 22.2, 21.5; HRMS-ESI C$_{15}$H$_{23}$O$_2$ [M+H$^+$] Calculated: 235.1693; Found: 235.1695

Synthesis of Compound C

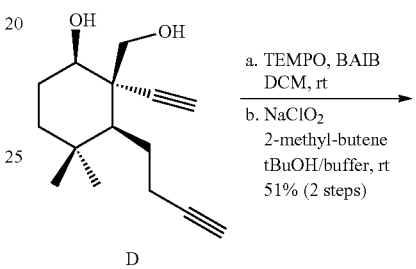

TEMPO (2,2,6,6-tetramethyl-piperidin-1-yl)oxy free radicals) (0.16 g, 1.03 mmol) and BAIB (iodobenzene diacetate) (0.56 g, 1.74 mmol) were added to Compound D (0.34 g, 1.45 mmol) in DCM solution (14 mL) at room temperature. Stirred the reaction system for 12 hours and saturated Na$_2$S$_2$O$_3$ aqueous solution was used to quench the reaction. The aqueous phase was extracted with DCM, the organic phases were combined and dried, concentrated by rotary evaporation, and purified by column chromatography (EtOAc/hexane=1/8) to get colorless oily liquid.

The product obtained from previous step was dissolved in tBuOH (8 mL) and phosphate buffer solution (pH=6.8, 8 mL), NaClO$_2$ (1.05 g, 11.6 mmol) and 90% isobutylene (4.3 mL, 36.3 mmol) were added at room temperature. Stirred the reaction system for 15 hours and the aqueous phase was extracted with EtOAc (6 mL×3). The organic phases were combined and dried, concentrated by rotary evaporation and purified by column chromatography (EtOAc/hexane=1/2) to get 0.185 g yellow solid, 51% for the two steps.

IR (neat, cm$^{-1}$): 3297, 2962, 2870, 2118, 1709, 1460, 1392, 1370, 1264, 1229, 1071, 932, 640; $^1$H NMR (500 MHz, CDCl$_3$) δ 7.52 (br.s, 1H), 3.70 (dd, J=11.9, 4.4 Hz, 1H), 2.49 (br, 1H), 2.37 (s, 1H), 2.43-2.30 (m, 2H), 2.03-1.92 (m, 1H), 1.97 (t, J=2.7 Hz, 1H), 1.89-1.80 (m, 1H), 1.76 (ddt, J=14.9, 9.8, 5.4 Hz, 1H), 1.50 (dt, J=13.7, 3.7 Hz, 1H), 1.42 (t, J=4.3 Hz, 1H), 1.34 (td, J=13.6, 4.0 Hz, 1H), 0.96 (s, 3H), 0.81 (s, 3H); $^{13}$C NMR (126 MHz, CDCl$_3$) δ 174.6, 84.5, 83.9, 77.3, 72.3, 68.6, 53.8, 51.1, 39.3, 34.6, 31.6, 27.6, 27.6, 21.3, 20.7; HRMS-ESI $C_{15}H_{21}O_3$ [M+H$^+$] Calculated: 249.1485; Found: 249.1488.

Synthesis of Compound B:

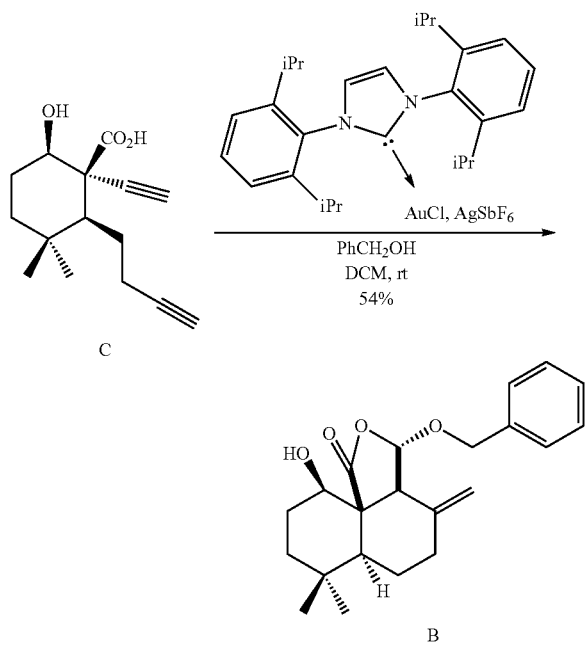

(IPr)AuCl (18.6 mg, 0.03 mmol), benzyl alcohol (93 μL, 0.9 mmol) and AgSbF$_6$ (10.3 mg, 0.03 mmol) were added to Compound C (74.5 mg, 0.3 mmol) in DCM solution (6 mL) at room temperature. Stirred the reaction system for 1 hour and the solution was concentrated by rotary evaporation, purified by column chromatograph (EtOAc/hexane=1/10) to yield 58 mg while solid, 54% yield.

IR (neat, cm$^{-1}$): 3486, 2949, 2869, 1778, 1455, 1357, 1144, 1086, 967, 740, 698; $^1$H NMR (500 MHz, CDCl$_3$) δ 7.35 (q, J=6.4, 5.9 Hz, 5H), 5.19 (s, 1H), 4.93 (d, J=10.7 Hz, 2H), 4.88 (d, J=2.2 Hz, 1H), 4.60 (d, J=11.2 Hz, 1H), 3.79 (d, J=1.7 Hz, 1H), 3.60-3.53 (m, 1H), 2.95 (s, 1H), 2.30 (ddt, J=13.8, 11.3, 2.5 Hz, 1H), 2.19 (td, J=14.9, 13.3, 6.4 Hz, 1H), 2.07 (tdd, J=14.2, 11.5, 3.1 Hz, 1H), 1.85-1.73 (m, 1H), 1.73-1.66 (m, 1H), 1.63-1.52 (m, 2H), 1.30 (ddd, J=26.8, 13.7, 4.2 Hz, 2H), 1.17 (s, 3H), 0.90 (s, 3H); $^{13}$C NMR (126 MHz, CDCl$_3$) δ 175.6, 143.5, 135.7, 128.8, 128.5, 128.4, 114.0, 103.9, 77.8, 71.1, 60.8, 55.0, 44.6, 39.5, 32.9, 32.5, 27.0, 26.3, 21.9, 20.6; HRMS-ESI $C_{22}H_{29}O_4$ [M+H$^+$] Calculated: 357.2060; Found: 357.2066.

Synthesis of Compound A:

Sodium (23 mg, 1 mmol) was added to liquid ammonia (3 ml) at −78° C., stirred for 0.2 hour. Then, Compound B (18 mg, 0.05 mmol) in THF solution (2.4 mL) was added dropwise. Stirred the reaction system for 0.6 hour and saturated NH$_4$Cl aqueous solution (2 mL) was used to quench the reaction. The aqueous phase was extracted with EtOAc (2 mL×2), the organic phases were combined and dried, concentrated by rotary evaporation to yield the crude product.

The crude produce was dissolved in MeOH (2.5 mL), at room temperature 5 M HCl solution was added to the reaction system, pH=2. Stirred the reaction solution for at 50° C. for 3 hours and saturated NaHCO$_3$ aqueous solution (2 mL) was used to quench the reaction. The aqueous phase was extracted with EtOAc (3 mL×3), the organic phases were combined and dried, concentrated by rotary evaporation, purified by column chromatography (EtOAc/hexane=1/6) to yield 57 mg white solid, 71% yield for the two steps.

IR (neat, cm$^{-1}$): 3428, 2958, 2928, 2854, 1765, 1746, 1382, 1261, 1161, 1055, 802; $^1$H NMR (500 MHz, CDCl$_3$) δ 4.79 (t, J=1.8 Hz, 1H), 4.77 (t, J=1.9 Hz, 1H), 4.57 (t, J=8.7 Hz, 1H), 4.00 (dd, J=8.8, 2.5 Hz, 1H), 3.62-3.55 (m, 1H), 3.16 (dt, J=8.7, 2.3 Hz, 1H), 2.43-2.34 (m, 1H), 2.30 (ddt, J=14.5, 11.4, 2.7 Hz, 1H), 2.19 (dtd, J=13.5, 11.7, 11.1, 2.5 Hz, 1H), 1.77 (ddt, J=16.5, 11.3, 5.6 Hz, 1H), 1.65-1.52 (m, 3H), 1.34 (dd, J=13.0, 4.5 Hz, 2H), 1.16 (s, 3H), 0.91 (s, 3H); $^{13}$C NMR (126 MHz, CDCl$_3$) δ 177.7, 147.0, 112.1, 79.3, 71.6, 54.9, 53.4, 45.4, 40.0, 33.0, 32.7, 28.5, 27.0, 22.0, 20.9; HRMS-ESI $C_{15}H_{23}O_3$ [M+H$^+$] Calculated: 251.1642; Found: 251.1648.

Synthesis of Natural Product Antrocin:

At −78° C., NaHMDS (Bis (trimethylsilyl)amide) (2 M) in THF, 33 μL, 0.066 mmol) was added dropwise to Compound A (11 mg, 0.044 mmol) in THF solution (2 mL). Stirred at 0° C. for 0.5 hour, carbon disulfide (8 μL, 0.132 mmol) was added. Stirred at room temperature for 1 hour and then MeI (19 μL, 0.308 mmol) was added. Stirred the reaction solution for 2 hours and saturated NH$_4$Cl aqueous solution (2 mL) was used to quench the reaction. The aqueous phase was extracted with EtOAc (3 mL×2), organic phases were combined and dried, concentrated by rotary evaporation, and purified by column chromatography (EtOAc/hexane=1/30) to yield an oily product.

The oily product was dissolved in toluene (2 mL), at room temperature nBu$_3$SnH (23 µL, 0.088 mmol) was added. The mixture was heated to 110° C. and then AIBN (azobisisobutyronitrile) (2 mg) was added. Stirred the reaction system for 1 hour and the solution was cooled to room temperature, concentrated by rotary evaporation, purified by column chromatography (EtOAc/hexane=1/30) to yield 8 mg natural product antrocin, 78% yield for the two steps.

IR (neat, cm$^{-1}$): 2934, 2854, 1768, 1457, 1375, 1368, 1190, 1121, 1055, 894; $^1$H NMR (500 MHz, CDCl$_3$) δ 4.84 (s, 1H), 4.81 (s, 1H), 4.48 (dd, J=9.5, 6.8 Hz, 1H), 4.15 (dd, J=9.5, 1.5 Hz, 1H), 2.67 (d, J=6.8 Hz, 1H), 2.42-2.31 (m, 1H), 2.25 (ddd, J=14.3, 8.6, 5.5 Hz, 1H), 2.20-2.11 (m, 1H), 1.80 (dddd, J=13.6, 10.7, 6.8, 3.5 Hz, 2H), 1.61-1.50 (m, 2H), 1.48 (dq, J=14.0, 3.3 Hz, 1H), 1.44-1.32 (m, 2H), 1.23 (dd, J=13.6, 3.3 Hz, 2H), 1.19 (s, 3H), 0.94 (s, 3H); $^{13}$C NMR (126 MHz, CDCl$_3$) δ 178.3, 146.8, 111.2, 69.4, 54.3, 48.5, 46.8, 42.1, 37.0, 33.3, 33.2, 30.4, 22.4, 22.2, 18.8; HRMS-ESI C$_{15}$H$_{23}$O$_2$ [M+H$^+$] Calculated: 235.1693; Found: 235.1699.

Example 2

Biological Activity Analysis of Antrocin (A) Activation of Frozen Cells

To activate frozen cells, quick thawing is the key to avoid re-crystallization of ice crystals which harm cells leading to cell death. After the frozen cells are activated, it takes several days or requires to subculture one to two generations before the frozen cells return to normal (for example, to produce monoclonal antibodies or other proteins). To quickly thaw the frozen cells, the frozen vial was removed from liquid nitrogen or dry ice container, and immersed in a 37 C water bath. Shook the frozen vial gently so that it melted in 3 minutes, wiped the vial with 70% alcohol and transferred the vial to a sterile workbench. The thawed cell suspension was removed and added slowly to a Petri dish filled with growth medium (dilution ration of 1:10-1:15), mixed thoroughly and placed the dish in a CO2 incubator. The growth medium was replaced with new growth medium the next day.

(B) Human Lung Cancer Cell Lines and Culture

Human lung cancer cell lines (CL1-0, CL1-5, H1975, H441, PC9, A549) and human bronchial epithelia cell lines (BEAS-2B) were obtained from the Institute of Clinical Medicine, Taipei Medical University. The cells were grown and maintained in DMEM medium (Dulbecco's Modified Eagle's Medium and RPMI basal medium supplemented with 10% fetal bovine serum, 2 mM glutamine, 1100 µg/ml streptomycin, and 100 U/ml penicillin in a wet incubator at 5% CO$_2$.

(C) Pharmaceutical Drug Treatment of Lung Cancer Cells

Lung cancer cell were grown in a medium supplemented with 10% fetal bovine serum until the cells grew to approximately 80% of their full-blown size. Old culture solution was drained, the lung cancer cells were washed with PBS buffer solution (phosphate buffered saline), and 10 ml of serum-free culture medium was added. Different pharmaceutical drugs were added according to experimental purposes, all reactions were carried out in an incubator at 37° C.

(D) Cytotoxicity

Human lung cancer cells (CL1-0, CL1-5, H1975, H441, PC9, A549) and human bronchial epithelial cells (BEAS-2B) were seeded in 96-well culture plates (2000 cells/well) and incubated overnight in 100 µl complete DMEM. Equal amount of complete DMEM sample containing 50 µl antrocin (0.5-10 µM) was placed in other wells of the culture plates. Further, 100 µl complete DMEM sample was also placed in wells as the control group. After two days, total number of human cells in each well was measured using sulforhodamine B (a fluorescent protein dye). Briefly, human cells were fixed in 10% trichloroacetic acid and stained with 0.4% sulforhodamine B. After being stained for 20 minutes, the human cells were washed with 1% acetic acid, and then sulforhodamine B, which was bound with human cells, was dissolved in 10 mM tris base. The optical density was measured at 562 nm by a microtiter plate detector. The aforementioned method was also used to determine the sensitivity of human CL1-0, CL1-5, H1975, H441, PC9, A549 and BEAS-2B cells to antrocin.

(E) Apoptosis

After being treated with antrocin, H441 cells were treated with trypsin-ethylenediamine tetraacetic acid (trypsin-EDTA), collected together with the culture solution, centrifuged to remove the supernatant, and washed in 4° C. phosphate buffered solution. After adding 1 ml ice-cold 75% ethanol, H441 cells were placed in a refrigerator overnight at 4° C. to be fixed. After centrifugation, H441 cells were suspended in 1 ml PBS, an appropriate amount of ribonuclease A (RNase A) was added, and H441 cells were let to sit for 30 minutes at 37° C. for reaction. Finally, 40 mg/ml propidium iodide (PI, Sigma Chemical Co., cat. No. p-4170) was added and H441 cells were let to sit for another 30 minutes for dark reaction. H441 cells were then collected by using a 35 mm nylon mesh, excited at a wavelength of 495 nm, and the fluorescence intensity of H441 cells was detected and analyzed at a wavelength of 637 nm by a flow cytometer.

(F) Bioluminescence Imaging (BLI)

Firefly luminescence genes (firefly luciferase) was introduced into H441 lung cancer stem cells by transgenesis, lung cancer cells (containing firefly luminescence genes) were then isolated from H441 lung cancer stem cells by FACS (Fluorescence-activated cell sorting) and implanted into immunodeficient mice subcutaneously or into the circulation system via the tail vein. IVIS imaging system (IVIS® Imaging System 200 Series, Xenogen) was used in the present embodiment for bioluminescent imaging. All mice were introduced with 150 mg/kg D-luciferin by intraperitoneal injection, after 10 minutes the mice were fixed in the darkroom of the IVIS200, the highly sensitive CCD camera of the IVIS 200 was used to detect the cold light radiated by firefly luminescence genes in H441 cancer cells. All mice were imaged for 120 seconds and the imaging time was shortened when the signal strength was saturated. All mice were anesthetized (2% isoflurane and 98% oxygen gas) and unconscious throughout the entire imaging process. Tumor sizes and signal strength radiated by the cold-light were compared and analyzed by using a software package of the IVI200. The inhibitory effect of antrocin on human lung cancer cells was assessed by using this bio-illumination-imaging system.

Antrocin Inhibits the Proliferation of Human NSCLC Cells.

Previous study demonstrated that natural antrocin inhibited the cell proliferation in breast cancer cells. (Rao et al., 2011). The present invention further studied the inhibitory effect of the chemically synthesized antrocin on the proliferation on NSCLC cells. As shown in FIG. 4 (A), the effectiveness of the chemically synthesized antrocin on the inhibition of cancer cell proliferation varied in different non-small cell lung cancer cell lines (NSCLC), the most robust inhibitions were observed in H1975 and H441 cell lines. The chemically-synthesized antrocin had significant inhibitory effect on cancer cell proliferation but no cytotoxicity against normal human bronchial epithelial cells.

We further studied H1975 and H441 cells to determine whether the inhibitory effect of chemically synthesized antrocin on the cell proliferation of lung cancer cells was related to the induction of apoptosis in lung cancer cells. As shown in FIG. 4 (B), antrocin treatment for 48 hours resulted in increase in the number of cells in early and late stage of apoptosis in a dose-dependent fashion. These results provided evidence that the chemically synthesized antrocin induced apoptosis in human NSCLC cells.

Antrocin Inhibits the Expression of Inflammatory Response-associated Genes in H441 Cells.

The present invention further investigated the effect of antrocin on cancer cells at the genetic level. After H441 cells had been treated with 5 μM antrocin for 12 hours, the effect of Antrocin on genetic transcription was analyzed. Only those genes whose expressions were inhibited 3.5 times or more were analyzed as target genes by GeneSpring software package and the results were presented using a tree diagram. STRING9.0 software package was also used to predict the effect of antrocin on the signaling pathway of H441 cells and possible target genes to be inhibited (FIG. 5). The results showed that more than 100 genes whose expressions were significantly affected by antrocin. These genes play important roles in cell proliferations, inflammatory responses, metastases, invasions, angiogenesis, and cell cycle regulations. Table 1 summarizes those genes whose expressions were significantly inhibited by antrocin treatment. These genes are associated with transcription factor NF-kB, for example cytokines (1F144, IFIT1, MX1), inflammatory responses (NFkB1 and IFIT2), stem cell properties (CT-NNBL1, SENP2, CEACAM1 and POU5F2), and drug resistance reactions (ABCB5, ABCG2 and XAF1), etc. Based on the aforementioned microarray results, the present invention further investigated inflammatory responses, stem cell properties, and multidrug resistance-associated protein expressions.

Antrocin Inhibits the Cell Proliferation of H441 Cells by Activation of Caspases-3 Enzyme, and Inhibition of XIAP, NF-kB-p65 and Cyclin D1 Expressions.

Antrocin inhibited cell proliferation of highly metastatic H441 cells. As the drug dose increased, antrocin markedly activated caspase enzyme 3 inducing apoptosis in H441 cells (FIG. 6). In addition, antrocin also dose-dependently inhibited the expression of inflammatory response-associated proteins, including XIAP, NF-kB-p65 and cyclin D1.

Antrocin Significantly Inhibits the Proliferation of Cancer Cells In Vivo.

The present invention further investigated the anticancer effect of antrocin in vivo. H441-L2G cells expressing firefly luciferase and green fluorescent protein were implanted by intravenous injections via the lateral tail vein (6×10$^5$/100 μl PBS) into non-obese diabetic/severe combined immunodeficiency mice. Daily intraperitoneal injections of antrocin (two groups of mice, a small dose of 5 mg/kg/day and a large dose of 10 mg/kg/day) were given over a period of four weeks to observe tumor growth. Tumor growth was inhibited after two weeks in half of the mice given small dose of antrocin. At the third week, tumor growth was observed in most of these mice (FIG. 7 (A), (B)). There was no significant difference in the body weight between the group treated with antrocin and the control group (FIG. 7 (C)).

With respect to survival rate, the median was 28 days for the control group and longer than 50 days for the treated group. 75% of the mice treated with small dose of antrocin at 5 mg/kg/day survived for longer than 50 days. At the end of the experiment (the fiftieth day) the median survival time increased by at least 60% (FIG. 7 (D)).

While preferred embodiments of the present invention have been shown and described, it is understood that the invention is not limited thereto because modifications may be made by those skilled in the art, particularly in light of the foregoing teachings. It is therefore contemplated by the appended claims to cover such modifications and incorporate those features which come within the spirit and scope of the invention.

What is claimed is:

1. A method for preparing antrocin, comprising the steps of:

(a) reacting Compound A

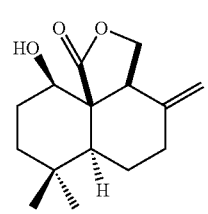

with sulfide and haloalkane in the presence of a base to produce an intermediate; and (b) reacting the intermediate with a free radical initiator and a free radical source to form antrocin.

2. The method of claim 1, wherein the base is sodium bis(trimethylsily)pamide, the sulfide is carbon disulfide, the haloalkane is iodomethane, the free radical initiator is azo-bis-isobutyronitrile, and the free radical source is tri-n-butyl-tin hydride.

3. The method of claim 1, wherein the Compound A is produced by reacting Compound B

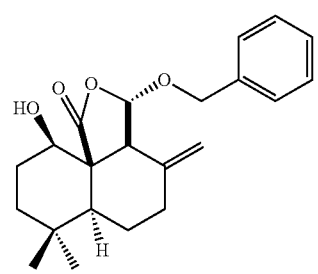

with an acid via a reducing agent.

4. The method of claim 3, wherein the reducing agent is an alkali metal, and the acid is hydrochloric acid.

5. The method of claim 3, wherein the Compound B is produced by reacting Compound C

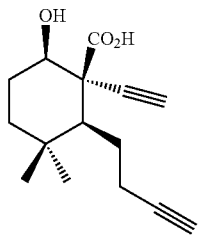

C with alcohol in an organic solvent in the presence of gold compound and silver salt as catalysts.

6. The method of claim 5, wherein the gold compound is a gold compound (IPr)AuCl having the following structure:

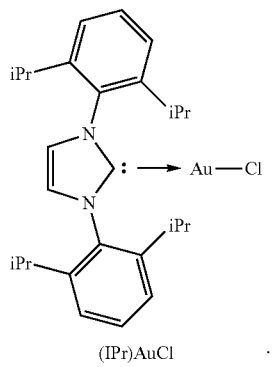

(IPr)AuCl

7. The method of claim 5, wherein the silver salt is AgSbF6, and the organic solvent is dichloromethane.

8. The method of claim 5, wherein the Compound C is produced by reacting Compound D

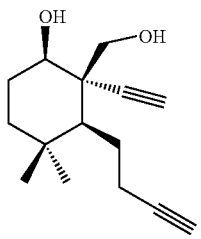

D with a first-step oxidizing agent and then reacting with a second-step oxidizing agent in a cosolvent.

9. The method of claim 8, wherein the first-step oxidizing agent is (2,2,6,6-tetramethylpiperidin-1-yl)oxy free radical and iodobenzene diacetate, the second-step oxidizing agent is sodium chlorite, and the cosolvent is t-butanol and an aqueous phosphate buffer solution of pH 6.8.

10. The method of claim 8, wherein the Compound D is produced by reacting Compound E

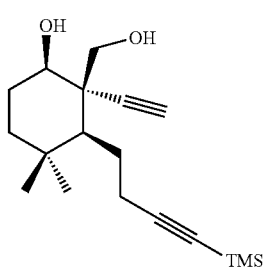

E with a base in a solvent.

11. The method of claim 10, wherein the base is potassium hydroxide and the solvent is a mixed solvent of methanol, tetrahydrofuran and water.

12. The method of claim 10, wherein the Compound E is produced by reacting Compound F

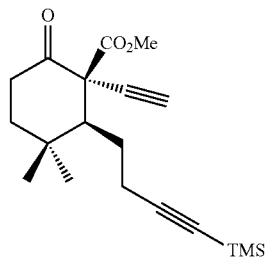

F with a reducing agent.

13. The method of claim 12, wherein the reducing agent is lithium aluminum hydride.

14. The method of claim 12, wherein the Compound F is produced by reacting Compound G

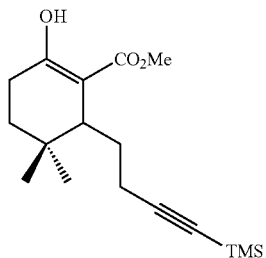

G with hypervalent iodine compound under the effect of a fluorine source.

15. The method of claim 14, wherein the hypervalent iodine compound is a compound having the following structure:

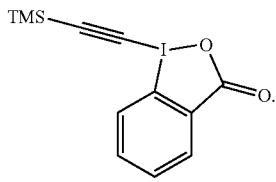 [SMILES: C[Si](C)(C)C#CI1OC(=O)c2ccccc21]

16. The method of claim 14, wherein the fluorine source is tetra-n-butylammonium fluoride in tetrahydrofuran solution.

17. The method of claim 14, wherein Compound G is produced by reacting Compound H

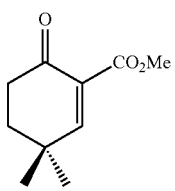

H with a Grignard reagent under the effect of a copper reagent.

18. The method of claim 17, wherein the Grignard reagent is prepared by a bromide having the following structure:
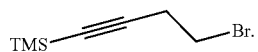
19. The method of claim 17, wherein the cooper reagent is cuprous bromide-dimethyl sulfide complex.
* * * * *